(12) United States Patent
Van Tuyl et al.

(10) Patent No.: US 7,426,866 B2
(45) Date of Patent: Sep. 23, 2008

(54) ACOUSTIC LIQUID DISPENSING APPARATUS

(75) Inventors: Michael R. Van Tuyl, San Jose, CA (US); James Chiao, Saratoga, CA (US); Michael J. Herrmann, San Jose, CA (US); Andrew M. Rose, Mountain View, CA (US)

(73) Assignee: EDC Biosystems, Inc., Milpitas, CA (US)

( * ) Notice: Subject to any disclaimer, the term of this patent is extended or adjusted under 35 U.S.C. 154(b) by 464 days.

(21) Appl. No.: 11/296,131

(22) Filed: Dec. 7, 2005

(65) Prior Publication Data

US 2006/0144871 A1 Jul. 6, 2006

Related U.S. Application Data

(60) Provisional application No. 60/638,558, filed on Dec. 22, 2004.

(51) Int. Cl.
*G01H 5/00* (2006.01)
*G01S 15/00* (2006.01)

(52) U.S. Cl. .......................... 73/597; 222/420; 73/589; 73/599; 73/64.53; 73/32 A

(58) Field of Classification Search ................ 73/597, 73/589, 599, 602, 64.53
See application file for complete search history.

(56) References Cited

U.S. PATENT DOCUMENTS

| | | | | |
|---|---|---|---|---|
| 3,985,030 A | 10/1976 | Charlton | | |
| 4,130,018 A | * | 12/1978 | Adams et al. | 73/290 V |
| 4,524,621 A | | 6/1985 | Yamanaka | |
| 4,545,245 A | | 10/1985 | Sharp | |
| 4,933,915 A | | 6/1990 | Bostrom | |
| 5,095,748 A | * | 3/1992 | Gregory et al. | 73/290 V |
| 5,121,340 A | | 6/1992 | Campbell et al. | |
| 5,263,371 A | * | 11/1993 | Maresca et al. | 73/290 V |
| 5,303,585 A | * | 4/1994 | Lichte | 73/290 V |

(Continued)

OTHER PUBLICATIONS

Masahiro et al., Ultrasonic Microscope, English Abstract of JP3090856, Apr. 16, 1991, one page, esp@cnet database.

(Continued)

*Primary Examiner*—Hezron E. Williams
*Assistant Examiner*—Samir M. Shah
(74) *Attorney, Agent, or Firm*—Donald J. Pagel

(57) ABSTRACT

A liquid dispensing apparatus for dispensing droplets of a liquid, and methods for measuring various fluid parameters of the liquid are described. The liquid dispensing apparatus comprises a container having a chamber for holding a liquid. An orifice is positioned at an end of the chamber for dispensing droplets of the liquid, the orifice being configured to retain the liquid in the container if the container is positioned with the orifice facing in a downward direction. An acoustic transducer means is at least partially positioned in the chamber for periodically propagating a focused acoustic beam toward the orifice and through at least some of the liquid while the liquid is contained in the chamber, with the focused acoustic beam being capable of causing a droplet of the liquid to be ejected from the orifice when a free surface of the liquid is within the depth of field of the acoustic transducer means. Fluid parameters that can be measured include the sound velocity in the liquid, liquid level and liquid concentration, liquid acoustic impedance, liquid density and ultrasonic viscosity.

8 Claims, 4 Drawing Sheets

U.S. PATENT DOCUMENTS

| | | |
|---|---|---|
| 5,604,301 A | 2/1997 | Mountford et al. |
| 5,880,364 A | 3/1999 | Dam |
| 6,047,600 A | 4/2000 | Ottosson et al. |
| 6,234,023 B1 | 5/2001 | Collins et al. |
| 6,357,671 B1 | 3/2002 | Cewers |
| 6,536,275 B1 | 3/2003 | Durkee et al. |
| 6,596,239 B2 | 7/2003 | Williams et al. |
| 6,623,700 B1 * | 9/2003 | Horine et al. ............... 422/100 |
| 6,713,022 B1 | 3/2004 | Noolandi et al. |
| 6,719,449 B1 | 4/2004 | Laugharn, Jr. et al. |
| 6,786,090 B2 | 9/2004 | Benghezal et al. |
| 6,925,870 B2 * | 8/2005 | Pappas et al. ............. 73/290 V |
| 2002/0125424 A1 * | 9/2002 | Ellson et al. ................ 250/288 |
| 2005/0150291 A1 | 7/2005 | Voss |
| 2005/0193805 A1 | 9/2005 | Williams et al. |

OTHER PUBLICATIONS

Doernhoefer, Thomas, Level Measurement, esp. in vehicle engine sump, English Abstract of DE4025326, Nov. 11, 1991, one page, esp@cnet database.

Brown, Albert E., Rationale and Summary of Methods for Determining Ultrasonic Properties of Materials at Lawrence Livermore National Laboratory, Apr. 25, 1997, pp. 1-45.

* cited by examiner

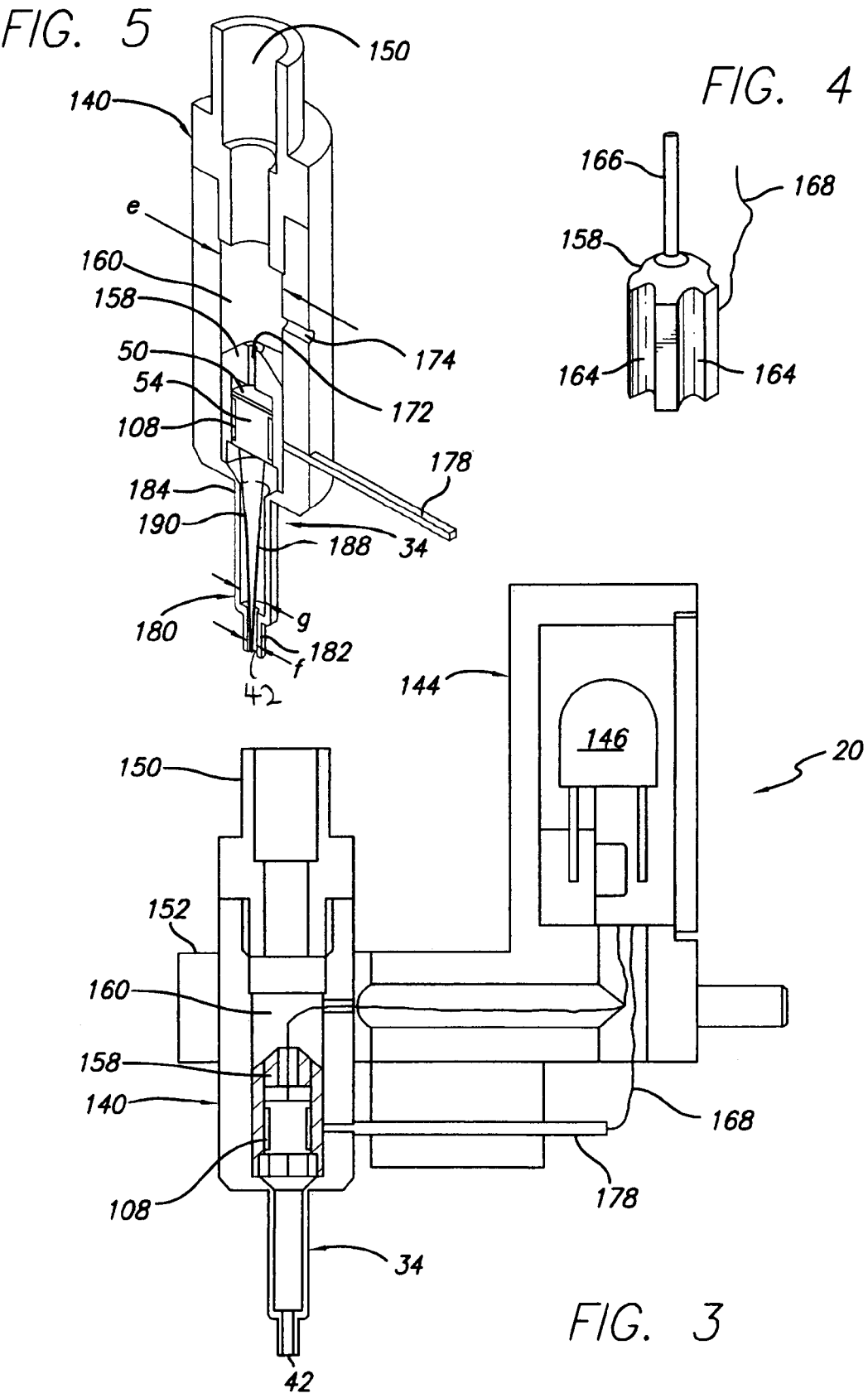

333# ACOUSTIC LIQUID DISPENSING APPARATUS

This application claims the benefit of priority of U.S. Provisional Patent Application 60/638,558, filed Dec. 22, 2004, which is incorporated herein by reference.

BACKGROUND OF THE INVENTION

1. Technical Field

The present invention relates to small-volume liquid dispensing technology, and more particularly to technology that uses acoustic energy to cause droplets of the liquid to be dispensed.

2. Background Information

Many methods for precision transfer and handling of liquids are known and used in a variety of commercial and industrial applications. A common method for high throughput precision liquid transfer is contact printing/deposition. However, contact printing requires the direct contact of a transfer device with the target surface, thus increasing the risk of contaminating the source liquid and/or its deposition interface. Cross-contamination is particularly problematic for biotechnology and biopharmaceuticals processes where ultra-pure liquid handling and transfer techniques are required. Not only is purity a concern, current biotechnological screening and manufacturing methods also require high throughput to efficiently conduct screening of compound libraries, synthesis of screening components, and other similar biochemical processes.

Liquid transfer methods that require contacting the target surface not only increase the likelihood of contamination, but also decrease the rate of liquid transfer. Because precision contact needs to be achieved between the print-head and the target surface, elaborate mechanical controls and/or cleaning mechanisms are usually required. This complex machinery may not conveniently and reliably produce high-density arrays. For example, in the manufacturing of high density microarrays, a sophisticated mechanical system would be required to control the print-head for contact with the target surface in the printing process. The mechanical movement of the print head to and from the target surface may increase liquid transfer time and limit system accuracy. The precision mechanical parts that are necessary to support movement of the print head may also increase system failure rate. Many biotechnology procedures require high throughput precision transfer of liquid, and have low tolerances for contaminations. Accordingly, a noncontact method for liquid transfer may be desirable.

Various non-contact printing/deposition techniques have been previously developed to overcome the limitation of contact printing techniques. Two common approaches are piezoelectric printing and syringe-solenoid printing. Piezoelectric printing may lead to the capturing of air bubbles in the output droplet. In addition, the droplet size is dependent on the size of the orifice. Thus, to generate microliter droplets, the size of the output orifice would typically be in the micron range. An output nozzle with a small orifice is susceptible to clogging. In addition, one may need to replace the nozzle in order to modify the droplet output size. In applications where multiple source liquids are being utilized, changing the source liquid may require replacement of the complete print-head, since typically the piezoelectric crystals are bonded with the output nozzle.

In a typical syringe-solenoid printing device, an electrically controlled mechanical valve is required to manage the liquid droplet output. This may result in large droplet size and slow liquid droplet ejection rate. In addition, a mechanical valve may be more prone to clogging and mechanical failure. In contrast, a liquid deposition apparatus that does not have a mechanically moving component in the liquid container may be more reliable.

Biotechnology screening techniques may involve many thousands of separate screening operations, with the concomitant need for many thousands of liquid transfer operations in which small volumes of liquid are transferred from a liquid source to multiple target sites. Similarly, biotechnology synthesis methods for the generation of tools useful for conducting molecular biology research often require many iterations of a procedure that must be conducted without contamination and with precision. Thus, a non-contact liquid transfer technique that allows precision transfer of liquids at high rate is desirable. In addition, a liquid transfer apparatus that allows the operator to control/modify the volume of liquid during the transferred procedure without changing or moving mechanical parts may provide various added advantages.

In order to meet these needs, methods have been developed utilizing acoustic waves to eject liquids out of source reservoirs. The acoustic droplet ejection systems allow for a non-contact method for the precision-transfer of small amounts of liquid in a rapid manner that is easily automated to meet industry needs. For example, U.S. Pat. No. 6,596,239, titled "ACOUSTICALLY MEDIATED FLUID TRANSFER METHODS AND USES THEREOF" issued to Williams et al., dated Jul. 22, 2003, is representative of the prior art. However, most of the prior art devices are configured to eject liquid in an upward direction. In various biological/chemical applications it is desirable to transfer liquid in a downward direction. For example, as mentioned earlier, to synthesize high density micro-array on a substrate, it may be desirable to deposit biologics or chemicals in a top down fashion.

Thus, an acoustic liquid deposition apparatus that is capable of transferring precision liquid droplets at a high rate is desirable. Preferably the apparatus may be adapted to eject liquid droplets in various directions and angles. It may also be desirable to adapt the apparatus to support on-the-fly modification of ejected liquid volume. Furthermore, for biological/chemical synthesis or screening applications, a built-in capability to characterize the physical parameters (e.g., concentration, density, viscosity, etc.) of the source liquid to be ejected may be particularly valuable.

SUMMARY OF THE INVENTION

Described herein is an acoustic liquid dispensing apparatus. The apparatus may be configured to eject droplet in various directions, including a top down arrangement where a focused acoustic beam is propagated downward into a contained volume of a source liquid to eject a droplet of liquid from a free surface. The apparatus may be further adapted to measure one or more parameters of the source liquid utilizing the acoustic transducer.

In one variation, the apparatus comprises a liquid container with an opening configured as a nozzle for dispensing liquid. An acoustic transducer is either attached to or positioned within the liquid container for propagating a focused acoustic wave to an orifice within said nozzle. Preferably, the orifice is small enough,. such that the capillary force and/or the atmospheric pressure will contain the source liquid within the liquid container when the orifice is placed in a downward direction (i.e., towards the ground and in the general direction of the gravitational force).

A pressure adjustment and/or a volume displacement mechanism may also be coupled to the liquid container to adjust the liquid pressure inside the liquid container, and prevent the source liquid from flowing out of the liquid container. The acoustic transducer may be fixed to the body of the container. Alternatively, the acoustic transducer is slidably positioned in relation to the liquid container. A diaphragm or other volume displacement device may be provided within the liquid container to control the liquid pressure within the liquid container. By adjusting the volume displacement device, the level of the liquid at the nozzle may be controlled.

An acoustic beam can be generated by the acoustic transducer and propagated toward the orifice at the nozzle. Preferably, the propagated acoustic beam focuses at or near the free surface of the source liquid where the source liquid in the liquid container interfaces the outside air. An acoustic wave feedback mechanism may be provided to measure the position of the liquid level at the nozzle. The focused acoustic energy forces a droplet of liquid to eject from the free surface along the direction of the acoustic beam.

In another aspect of the invention, a computer and feedback mechanism is provided to control the ejection of droplets of liquids. In order to dispense a precise liquid droplet with the acoustic beam focused on the free surface of the liquid, it is necessary to accurately know the distance from the free surface to the acoustic transducer. This distance can be measured acoustically if the sound velocity in the liquid is known. However, in many applications, the sound velocity is unknown. Furthermore, the sound velocity also may vary with temperature and with changes in concentration. Therefore, in order to put the free surface in focus, it is necessary to measure distance from the lens to the free surface of the liquid. And in order to measure this distance, it is necessary to measure the sound velocity in real time. This can be done by providing a calibration surface to reflect part of the transmitted beam at a known distance. The acoustic transducer may also be adapted to generate a test waveform toward the free surface. The test waveform typically consists of several cycles of sinusoidal wave. In one variation, a calibration surface is provided within the liquid container to reflect part of the focused acoustic beam propagated from the acoustic transducer. Since the distance between the acoustic transducer and the calibration surface is calibrated and known, one may calculate the sound velocity in the source liquid based on the distance and the time interval between the reflected acoustic waves from the lens and the calibration surface. Once the sound velocity in the liquid is known, by detecting the reflected wave back from the free surface of the liquid, the computer may determine the position of the liquid level. Furthermore, knowing the sound velocity in the given source liquid helps one calculate other associated parameters (e.g., concentration, density, viscosity, etc.) of the source liquid.

An optional temperature sensor may be provided in the container for measuring the temperature of the source liquid within the liquid container. By measuring the liquid temperature, any variation in sound velocity due to temperature can be compensated. In addition, given sound velocity and the temperature information, the concentration of the liquid may be determined based on previously calibrated data.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE SEVERAL VIEWS OF THE DRAWINGS

FIG. 3 is a schematic cross-sectional view illustrating another variation of an acoustic liquid dispensing apparatus according to the present invention;

FIG. 4 is a side elevation view of a waveguide housing according to the present invention;

FIG. 5 is a cross-sectional view illustrating part of the acoustic liquid dispensing apparatus shown in FIG. 3;

DETAILED DESCRIPTION OF THE INVENTION

Figure 1:
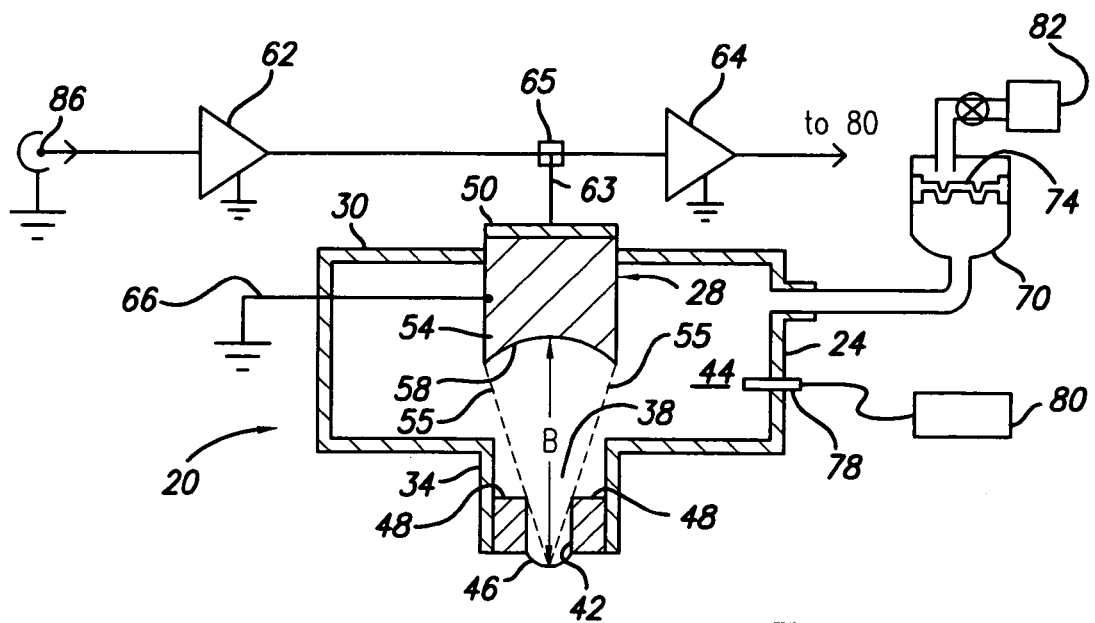
FIG. 1 is a schematic cross-sectional view of an acoustic liquid dispensing apparatus according to the present invention.

The following detailed description should be read with reference to the drawings, in which identical reference numbers refer to like elements through out the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that microarray printing is used herein as an exemplary application, and it is not intended to limit the scope of the application. In light of the disclosure herein, one of ordinary skill in the art would appreciate that variations of the invention may be applied in various application where dispensing of precision amounts of liquids at a high rate is desirable. Moreover, it should be understood that embodiments of the present invention may be applied in combination with various mechanical platforms and alignment systems for depositing droplets of liquids in an array fashion. It is also contemplated that the acoustic liquid dispensing apparatus described herein may be implemented for delivery of liquids containing various biological, biochemical and/or chemical compounds, such as liquids containing DNA, RNA, proteins, monoclonal antibodies, chemical catalysts, etc., all of which are referred to generally as source liquids.

It must also be noted that, as used in this specification and the appended claims, the singular forms "a," "an" and "the" include plural referents unless the context clearly dictates otherwise. Thus, for example, the term "a sensor" is intended to mean a single sensor or a combination of sensors, "a liquid" is intended to mean one or more liquids, or a mixture thereof.

In one aspect of the invention, the acoustic liquid dispensing apparatus comprises a liquid container with an integrated acoustic transducer. The liquid container comprises an orifice for ejecting a droplet of a source liquid contained within the container. The acoustic transducer is adapted to propagate a focused acoustic beam toward a free surface of the source liquid at the orifice to force a droplet of the source liquid to eject from the free surface. The acoustic transducer may be moveably or fixedly coupled to the liquid container. Furthermore, in a preferred configuration, the acoustic liquid dispensing apparatus is configured in a top down configuration with the liquid ejecting orifice facing downwards (in the general direction of the gravitational force). The liquid container is adapted to retain the source liquid within the container so as to prevent the source liquid from exiting the orifice without the excitation of an acoustic wave. Preferably, this is done by sizing the orifice in view of the surface tension of the source liquid. The acoustic transducer is configured to propagate a focused acoustic beam in the downward direction towards the liquid free surface in the orifice to eject a droplet of source liquid in the downward direction. The apparatus may be configured such that an ejected droplet's trajectory is downward and parallel to the gravitational force. Alternatively, the apparatus may be configured to eject liquids at an angle to the gravitational force, including a ninety degree, or even a one hundred and eighty degree angle to the gravitational force.

In one variation, an acoustic liquid dispensing apparatus 20 comprises a liquid container 24 with an acoustic transducer 28 connected to a proximal end 30 of the container 24 as shown in FIG. 1. The container 24 has a nozzle 34 extending from it. An inner lumen 38 in the nozzle 34 leads to an orifice 42 from which droplets are ejected out of the container 24. Preferably the inner diameter of the orifice 42 is between about 0.1 mm to about 2 mm; and more preferably between 0.2 mm to about 1.5 mm. In one example, the diameter of the orifice is 0.8 mm. The container 24 includes a chamber 44 where the source liquid is held. Preferably, the chamber 44 is just a hollow region within the container 24. The lumen 38 in the nozzle 34 is part of the chamber 44, but the nozzle 34 has a width less than the width of the chamber 44. When the container 24 is filled with the source liquid, a free surface 46 is formed at the orifice 42 where the source liquid interfaces with the environment outside the container. Depending on the surface tension at the free surface 46, the free surface may form a concave, convex, or flat surface. A calibration surface 48 is positioned inside of the nozzle 34.

In this variation, the acoustic transducer 28 comprises a piezoelectric crystal 50 (e.g., 20 MHz crystal, cylindrical in shape with a 1 mm active area) attached to the proximal end of a waveguide 54. Preferably, the waveguide 54 comprises aluminum and is a solid cylinder in shape. One of ordinary skill in the art would appreciate that the waveguide may be comprised of other acoustic conductive materials, such as silicon, silicon nitride, silicon carbide, sapphire, fused quartz, certain glasses, or many other acoustically conductive materials. The distal end of the waveguide is configured with a concave surface 58 which serves as the lens for focusing the acoustic wave into a focused beam for propagation through the source liquid. Preferably, the lens is configured to focus the acoustic wave at or near the free surface 46.

To achieve proper focus and to capture the maximum amount of energy emitted by the crystal 50, various geometrical and acoustic parameters should be selected as is described in U.S. Pat. No. 6,596,239. Specifically, it is preferred that the lens diameter be greater than the diameter of the crystal 50. In a preferred embodiment for producing relatively large drops, the focal distance B of the lens 58 is approximately 0.433 inches (11.0 mm). This yields an f-number of the lens 58 equal to approximately 11.1 (0.433/0.039=11.1), where f=B/D, and D is the diameter of the active area of the crystal 50, and D=0.039 inches (1.0 mm) in. a preferred embodiment. Thus, for large drops (e.g. drops in the range of three to five nanoliters), the f-number of 11.1 implies a long depth of field. This means that drops of source liquid can still be produced even when the free surface 46 moves towards or away from the lens 58 within a relatively large range.

For smaller drops (e.g. drops smaller than one nanoliter), it is preferred that the radius of curvature of the lens 58 (i.e. the focal distance B) be chosen to provide an f-number in the range of about one to four. In a preferred embodiment for producing small drops, B is approximately 0.125 inches (3.2 mm) and D is approximately 0.118 inches (3.0 mm). This yields an f-number of approximately 1.07 (0.125/0.118=1.07). This relatively small f-number implies that the depth of field is not very large, so the distance between the lens 58 and the free surface 46 must be controlled more carefully in order to produce drops with the apparatus 20. In general, the focal distance B can be anywhere in the range of one to twelve millimeters. Regardless, of the f-number being used, it is desirable to have control over the focusing of the apparatus 20. In some embodiments, this is done by controlling the liquid level of the source liquid in the nozzle 34 as is described later.

An external receptacle 70 may be provided for supplying the source liquid into the liquid container 24. A volume displacement device 74 (e.g., a diaphragm or plunger) may be positioned in the external receptacle 70 to control liquid flow into the liquid container 24. The volume displacement device 74 may also be utilized to control the liquid pressure within the liquid container. Other pressure generating devices may also be used in place of the volume displacement device 74, such as a device for injecting an inert gas into the external receptacle 70 to control the gas pressure. Alternatively, the liquid level in the nozzle 34 may be controlled by the raising or lowering of the external receptacle 70. A computer 80 may be implemented to control the volume displacement device 74 and/or the vertical position of the external receptacle 70, or the pressure generating device, and thereby manage the liquid level (i.e., the location of the free surface 46) in the nozzle 34.

In other embodiments, a volume displacement device may be placed within the liquid container 24 to control the liquid level within the nozzle 34. A temperature sensor 78 may be placed within the liquid container 24 to measure the temperature of the source liquid within the liquid container 24 and to provide temperature data to a computer 80. Alternatively, the temperature sensor 78 may comprise a remote sensing device such as an infrared pyrometer. Although in FIG. 1, the external receptacle 70 is utilized to supply the source liquid to the liquid container 24, the liquid container 24 may also be adapted to extract the source liquid from the nozzle 34. In this embodiment, suction may be provided to lower the pressure within the liquid container 24 while the tip of the nozzle 34 is placed within a source liquid pool to cause the source liquid to flow into the liquid container 24. The suction may be provided by a vacuum pump 82 or other low pressure generating device attached through a port on the liquid container 24 or the receptacle 70. Alternatively, a volume displacement device could be positioned within the liquid container 24 for generating low pressure (suction) to cause the source liquid to flow into the nozzle 34.

Since the apparatus utilizes a focused acoustic beam to eject liquids through an orifice, the size of the ejected droplet may be controlled through the amount of energy applied to the acoustic transducer by changing the amplitude and/or duration of the applied sinusoidal waveform. Generally, many cycles of a sine wave are sent from the amplifier 62 to the crystal 50 to generate an acoustic wave. This allows one to design an apparatus with a large orifice diameter, such as in the 0.2 to 1.5 mm range, while still being able to eject droplets (e.g., one nanoliter) of liquid through the large orifice opening. The ejected volume can be varied over a large range and is partly dependent on the frequency of the crystal 50. The volume of a droplet can range from five to twenty-five picoliters up to approximately one microliter, and volumes as small as one picoliter can probably be obtained. Furthermore, the frequency of droplet emission is very fast with frequencies of up to several kilohertz (several thousand drops/sec) being obtainable. Thus, the apparatus may be configured to eject varying volumes of the source liquid without changing tips.

Generally, the volume of source liquid droplets ejected from the nozzle 34 is controlled by selection of the crystal 50. Crystals with higher resonance frequencies yield smaller droplets. For a given crystal, the minimum energy (power times period) to produce an ejected droplet of the source liquid is determined. Then the energy is increased until unstable droplets of source liquid (i.e. inconsistent droplet volume and/or direction) are ejected from the nozzle 34. An energy value between the minimum and maximum energies is selected as the operating energy and the volume of a droplet produced under these conditions is determined. During subsequent operation of the acoustic liquid dispensing apparatus 20, uniform droplets of the determined volume will be produced for a given source liquid, provided that the proper energy setting is used. If a larger volume of source liquid is needed, multiple droplets can be dispensed in the same location. Additionally, a change in the f-number of the lens 58 will change the drop size, with a smaller f-number yielding a smaller drop size.

Referring to FIG. 1, an electric energy source 86 is provided to deliver energy through an amplifier 62 to excite the piezoelectric crystal 50. A transmission line 63, such as a coaxial cable, delivers pulses of alternating current generated by the amplifier 62 to the crystal 50. In applications where the piezoelectric crystal 50 is utilized for both generating and detecting acoustic waves, a receiver 64 may be provided to receive electrical signal from the piezoelectric crystal 50. Because the receiver 64 is sensitive and cannot withstand the large output from the amplifier 62, a means for protecting the receiver 64 from the amplifier output signal is needed. Preferably, this protection is provided by a broadband RF directional coupler 65 positioned between the amplifier 62 and the receiver 64 to separate the amplifier output from the input to the receiver 64 at all times. Alternatively, many other circuit designs that provide such protection to the receiver 64 may be used. A ground lead 66 connected to the waveguide 54 grounds the acoustic transducer 28 and is part of the transmission line 63. In one embodiment, the amplifier 62 comprises a class A linear amplifier, and the receiver 64 comprises digitizing signal capture device.

As discussed earlier, electronic circuitry may be provided to utilize the piezoelectric crystal 50 to detect reflected acoustic waves. The reflected acoustic waves provide information that is used to adjust the liquid level within the nozzle 34, and to calculate various parameters related to the physical properties of the source liquid, as is discussed later. In such a configuration, acoustic waves reflected off the free surface 46 of the source liquid at the orifice 42 may be used to determine the liquid level in the nozzle 34 provided that the sound velocity in the source liquid is known or measured. The acoustic waves reflected off the free surface 46 is detected by the piezoelectric crystal 50 and a corresponding electrical signal is transmitted to the receiver 64. After analog to digital conversion of the reflected signal, the computer 80, which is connected to the receiver 64, may use the reflected signal to calculate the location of the free surface 46 based on the time delay between the reflection of acoustic waves off the waveguide lens 58 and the detection of acoustic waves reflected off the free surface 46. The computer 80 may then be utilized to adjust the liquid level in the nozzle such that the liquid free surface 46 is within the depth of field of the focal distance of the acoustic beam. In one embodiment, the computer 80 comprises a microprocessor controlled computer such as a computer with a Pentium® microprocessor and the Windows® operating system. In other embodiments, the computer 80 may comprise a more dedicated type of electrical device such as a microcontroller, a digital signal processor (DSP), a field programmable gate array (FPGA), analog circuitry, a custom integrated circuit, or another type of device. All of these embodiments may be referred to as computing means.

The temperature sensor 78 functions to measure the temperature of the source liquid inside the liquid container 24. Since changes in temperature may substantially effect the physical characteristics (e.g., sound velocity, density, viscosity, etc.) of liquids, monitoring the temperature and other fluid properties of the liquid may allow the system to determine the amount of acoustic energy required to eject a droplet of liquid. Measuring the temperature and the sound velocity also allows the system to determine the concentration of a known liquid from a calibration table. Preferably, the temperature sensor is connected to the computer 80 as illustrated in FIG. 1. The computer 80 may then utilize the temperature information along with other liquid related data (e.g., liquid level, concentration, viscosity, etc.) to determine the preferred amount of electrical energy to use to excite the crystal 50, and thus provide the desired amount of acoustic energy towards the free surface 46.

In its simplest form, the apparatus 20 shown in FIG. 1 comprises the container 24 having the chamber 44 for holding the source liquid, and the single acoustic transducer 28. The orifice 42 is positioned at an end of the chamber 44 for dispensing droplets of the source liquid, and the orifice is configured to retain the source liquid in the container 24 if the container 24 is positioned with the orifice 42 facing in a downward direction. The apparatus 20 can be used when the orifice 42 is oriented in other directions, but regardless of the orientation of the orifice 42, it should retain the source liquid. Usually, it is the surface tension of the source liquid that holds the source liquid in the orifice 42. The acoustic transducer 28 is at least partially positioned in the chamber 44 for periodically propagating a focused acoustic beam toward the orifice 42 through at least some of the source liquid while the source liquid is contained in the chamber 44. The focused acoustic beam is capable of causing a droplet of the source liquid to be ejected from the orifice 42 when the free surface is within the depth of field of the acoustic transducer 28.

In FIG. 1, the acoustic transducer 28 is attached to a proximal end of the container 24 with the crystal 50 positioned outside of the container 24. In this configuration, the crystal 50 would preferably have some type of protective covering (not shown) to protect the crystal 50 from contamination. However, since the crystal 50 is not exposed to source liquid, the covering is not critical. The waveguide 54, which is in the chamber 44 and is immersed in the source liquid, must either be comprised of a material that is inert to the source liquid, or the waveguide 54 must be protected with a chemically inert covering. The waveguide 54 could also be positioned such that only the lens 58 is inside the chamber 44 and in contact with the source liquid.

Figure 2:
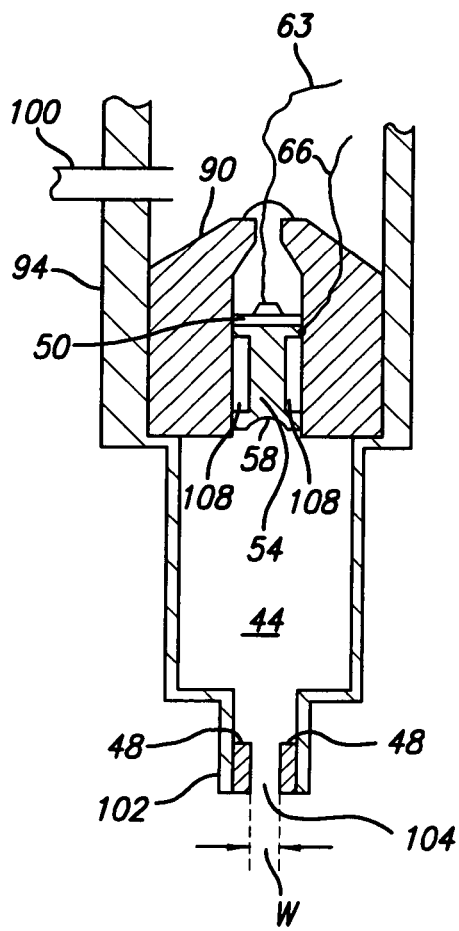
FIG. 2 is a schematic cross-sectional view illustrating another variation of an acoustic liquid dispensing apparatus according to the present invention.

In another variation, the acoustic transducer is placed within an acoustic transducer housing 90. The proximal end of a liquid container 94 is configured to receive the acoustic transducer housing 90, as shown in FIG. 2. The acoustic transducer housing 90 may be fixedly connected to the liquid container 94 with adhesives. The liquid container 94 is configured with a port 100 for receiving the source liquid. Channels in the waveguide housing 90 allow the source liquid to flow around the waveguide housing 90, as is discussed later with respect to FIG. 4. A nozzle 102 is provided at the bottom of the liquid container. The orifice 104 at the distal tip of the nozzle 102 is utilized to eject liquid droplets of the liquid container. The diameter (w) of the orifice 104 is the inner diameter of the nozzle 102 that is available for allowing a free surface of the source liquid to form, such as the free surface 42 shown in FIG. 1. As can be seen in FIG. 2, if the calibration surface 48 extends all the way down to the distal end of the nozzle 102, then the orifice 104 is the diameter of the channel bounded by the calibration surface 48.

Depending on the application, the inner surface of the nozzle may be coated with a hydrophilic or a hydrophobic coating. The hydrophilic or hydrophobic coating may be utilized to modify the surface tension of the liquid free surface when the source liquid level is within the nozzle. For example, to increase the liquid containers ability to retain liquid within the liquid container, one may implement a hydrophilic surface on the inner lumen of the nozzle. Generally, the nozzle 102 is cylindrical in shape and the orifice 104 is circular in shape. The diameter of the orifice 104 may also be modifying depending on design needs. A noncircular orifice 104 may also be utilized, such as a square orifice, a rectangular orifice or a triangular orifice. Preferably, an air gap 108 extends around the cylindrically shaped waveguide 54 to provide a pocket of air between the waveguide 54 and the waveguide housing 90. The air gap 108 reduces the acoustic energy loss through the side walls of the waveguide 54.

Many other configurations for the acoustic liquid dispensing apparatus 20 are possible. For example, the acoustic transducer housing 90 could be movable within the container 94, with the movement controlled by an electromechanical actuator. In this case, a second calibration surface would be needed because the distance between the lens 58 and the calibration surface 48 is not constant. By introducing a second calibration surface, positioned at a calibrated distance from the surface 48, the time between the between the echoes from the surface 48 and the second calibration surface can be used to determine the sound velocity. In other embodiments, the acoustic transducer 28 can be positioned in a chamber that is separated from the nozzle 102, and the acoustic energy is transmitted to the free surface 46 through a coupling medium, such as a liquid or paste.

In one particular design, shown in FIG. 3, the acoustic liquid dispensing apparatus 20 comprises a liquid dispensing unit 140 integrated with a housing 144 which contains electronic circuitry to supply electric power to the acoustic transducer 28. The housing 144 may be attached to a movable or stationary support frame. In this particular design the device is configured for a top down (i.e., ejecting liquid droplets in the general direction of the gravitational force) dispensing application. The liquid dispensing unit 140 may be secured to a stationary system while the target (e.g., wellplates, glass slides, etc.) are aligned with the tip of the liquid dispensing unit through electromechanically controlled platform. Alternatively, the target is secured at a stationary position while a precision electromechanical lever system is utilized to move the liquid dispensing unit over the target to dispense controlled amounts of droplets on a series of predefined locations on the target receiving device.

Mounting features are provided on the back of the housing 144 for securing the complete apparatus 20 onto a frame or a platform. The electronics within the housing 144 comprise a transformer (not shown) that is mounted behind an inductor 146, as well as other supporting electronic components. The electronics couple the power from the amplifier 62 to the apparatus 20 to excite the piezoelectric crystal 50. The electronics may be tuned to match the impedance characteristics of the piezoelectric crystal 50 at a specific frequency. In one particular design, the electronic circuit presents a fifty ohm impedance to the external drive circuit and passes an alternating current at approximately 20 MHz and passes an alternating current to drive the piezoelectric crystal. In other embodiments, the circuit parameters can be changed to function with other crystals and/or other circuit designs.

A fitting 150, such as a Luer Lock fitting, is provided at the top end of the liquid dispensing unit 140 for connection to a piece of tubing. The tubing delivers liquids from a liquid source to the liquid dispensing unit 140. For example, a piece of flexible tubing connected to the fitting 150 may be used to connect a pressurized liquid source to the liquid container. Other liquid source/reservoir may also be utilized to supply source liquids to the liquid dispensing unit through the fitting 150. Alternatively, a suction source may be connected to the fitting 150 such that negative pressure may be generated within the liquid container to uptake source liquid through the nozzle of the liquid container.

A housing clamp 152 is provided to secure the liquid dispensing unit 140 to the electrical housing 144. The liquid dispensing unit 140 comprises a liquid container with a waveguide housing 158 positioned within a lumen 160. Preferably, the liquid dispensing unit 140 is comprised of a chemically inert material such as polycarbonate or stainless steel so that it does not react with the source liquid. The acoustic transducer 28 is secured within the waveguide housing 158 and comprises the piezoelectric crystal 50 attached to the proximal end of the waveguide 54.

The waveguide housing 158, shown in more detail in FIG. 4, is configured with a plurality of channels 164 in the peripheral surface to permit liquids to flow from the proximal portion of the lumen 160, pass the waveguide housing 158, and into the distal portion of the lumen 160. In this particular design, the waveguide housing 158 comprises stainless steel. The waveguide housing 158 isolates the piezoelectric crystal from the source liquid inside the liquid dispensing unit 140. An electrical lead 166 delivers power to the crystal 50, and the electrical lead 168 completes the electrical circuit.

FIG. 5 illustrates the liquid dispensing unit 140 in more detail. In this embodiment, the crystal 50 comprises an approximately 20 MHz piezoelectric crystal. The electrical lead 166 is soldered to the top side of the piezoelectric crystal and is provided to direct electric current from the electronics in the electronic housing 144 to the piezoelectric crystal 50. A sealed (fluid tight) aperture 172 allows the lead 166 (shown in FIG. 4) to pass through the waveguide housing 158, and an aperture 174 allows the lead 166 to pass through the liquid dispensing unit 140. The bottom side of the piezoelectric crystal 50 may be plated with a conductive material (e.g., gold, silver, gold-chrome plate or other conducting materials) so that good electrical contact can be established with the waveguide 54. However, this is not essential because the waveguide side of the crystal 50 is capacitively coupled to the waveguide 54. In any event, good acoustic-mechanical coupling between the crystal 50 and the waveguide 54 is needed. Since the waveguide 54 is aluminum, it is conductive. The aluminum waveguide makes contact with the conductive waveguide housing 158 which is comprised of a conductive material such as stainless steel. To complete the electric circuitry to the piezoelectric crystal, a spring probe 168 (shown in FIG. 3) connected to ground wiring from the electronic components in the electronic housing 144 is used to provide the return electric path. The distal portion of the ground wiring is connected to a spring probe that is mounted on the side of the liquid dispensing unit 140. The spring probe is inserted through the liquid housing and contacts the conductive waveguide housing 158. A probe insulator 178 is provided to support the spring probe 168 and electrically isolate it from the housing of the apparatus 20.

In one particular application, the electronics may be configured to drive an approximately 20 MHz electric current onto the piezoelectric crystal. Depending on the design criteria, one of ordinary skill in the art would appreciate that piezoelectric crystals having other fundamental frequencies may also be implemented in the acoustic dispensing apparatus. For example, any piezoelectric crystal having a fundamental frequency in the range of one to sixty megahertz (1-60 MHz), or even higher, may be suitable. One may select the piezoelectric crystal based on the range of the desired liquid drop size to be ejected by the apparatus. Preferably, the crystal 50 comprises lead zirconate titanate (PZT) for applications of 20 MHz and less, and comprises lithium niobate for higher frequency applications.

Preferably, the waveguide comprises aluminum and the distal end of the waveguide has a concave profile forming a lens for focusing the acoustic energy generated by the piezoelectric crystal. The piezoelectric crystal may be bonded to the proximal end of the waveguide using an epoxy. A metallic waveguide may be implemented along with a metallic housing to facilitate dissipation of heat that is generated by the excited piezoelectric crystal. On of ordinary skill in the art would appreciate that other acoustically conductive materials (e.g., titanium, glass, ceramic, etc.) may also be adapted for utilization the apparatus to propagates and/or focus the acoustic wave. For low frequency applications, polymeric materials such as polycarbonate or Delrin™ acetal resin may also be applicable. Design alterations would be needed to provide the return or ground path for the crystal when the waveguide is not electrically conductive.

For liquid ejection purposes, one of ordinary skill in the art would appreciate that the distal end of the liquid dispensing unit 140 may have various profiles. However, in some applications, such as to extract liquid with the nozzle 34 of the liquid dispensing unit 140, it may be desirable to have a step-shaped tip on the distal end. In the variation shown in FIG. 5, the liquid container is configured with a step-shaped tip 180 such that it may be utilized to extract liquids from concaved reservoir (e.g., wells on a wellplate). A distal portion of the tip 180 is configured with a first tip portion 182 and has inner diameter f. A second tip portion 184 is positioned above the first tip portion 182 with the second tip portion 184 having an inner diameter g that is larger than the inner diameter f of the first portion 182. In this particular design, the first tip portion 182 is configured for insertion into the wells of a conventional 1536 wellplate, while the second tip portion 184 is configured to fit into the wells of a conventional 384 wellplate. Therefore, the outer diameter of the first tip portion 182 is smaller than the outer diameter of the second tip portion 184. The larger inner diameter g of the second tip portion 184 is required so that there is enough room for the focused beam to be focused at the orifice 42. The focused beam is illustrated by the traces 188 and 190, which illustrate that the first tip portion 182 would not be wide enough to accommodate the focused acoustic beam. The vacuum 82 (shown in FIG. 1) could be used to supply the reduced pressure to draw source liquid up into the tip 180 when the external receptacle 70 is not used for providing a supply of source liquid. Typically, the lumen 160 has an inner diameter e that is greater than the inner diameter g, so as to accommodate the waveguide 54.

Depending on the application needs, the liquid dispensing unit may be configured with or without the step-wise tip design (the steps in the step-wise tip are not necessarily the same as the steps in the calibration surface 48). One of ordinary skill in the art having the benefit of this disclosure would appreciate that the tip may also be configured with three or more steps to accommodate three or more types of wellplates or liquid reservoirs. The tip portion may also comprise of transparent polymeric material such that the operator may observe the liquid level inside the tip portion. For applications limited to liquid dispensing, such as depositing array of droplets on a piece of glass, an extension at the distal end of the liquid dispensing unit may not be necessary. Preferably, the inner surface of the orifice is configured to facilitate the formation of meniscus at the focal point of the focused acoustic beam. For example, a nozzle shaped profile may be provided to facilitate the formation of meniscus within the lumen of the nozzle. The meniscus provides a free surface for the acoustic beam to focus on to eject liquid droplets. For application where the liquids are dispensed into wells or concaved surfaces, a nozzle with a small diameter may be desirable such that the tip of the nozzle may be inserted into the well. A higher precision in the delivery location may be achieved if the tip of the nozzle is placed closed to the target surface. However, for application where a higher tolerance for precision is allowed, one may position the tip of the nozzle outside the well to dispense the liquid.

In an alternative design, the acoustic liquid dispensing apparatus is configured as a pen-like device. The modularized device may be handled by a lab technician with his or her own hands to dispense controlled amounts liquids onto a desired surface. The modularized device may have its own dedicated liquid source. Optionally, a flexible tube may be used to connect the dispensing device to a liquid source. Electrical wiring may be used to provide power to the modularized liquid dispensing device. Alternatively, the modular device may have its own built in rechargeable power supply. Electronic control circuitry, which is well known to one of ordinary skill in the art, may also be build into the modularized device for controlling the amount of acoustic energy applied to eject the liquid droplets.

In another design variation, a plurality of the liquid dispensing apparatuses 20 can be assembled, with each comprising a container 24 with its own corresponding acoustic transducer 28. The plurality of liquid dispensing apparatuses may be aligned in a one dimensional array configuration, a two dimensional array configuration, or even a three dimensional array. A computer controller may be implemented to simultaneous control the dispensing of liquid through the plurality of liquid dispensing units.

To precisely control the size of the liquid droplet to be ejected from the acoustic liquid dispensing apparatus, it is desirable to know the some of the properties of the source liquid, such as:

$\upsilon$—sound velocity of the acoustic wave in the source liquid
C—concentration
Z—liquid acoustic impedance
$\rho$—density of the liquid
a—ultrasonic attenuation in the liquid
$\eta$—ultrasonic viscosity
L—liquid level at the nozzle opening Since some of the liquid properties may change during the dispensing process, it is desirable to measure these properties in real time. Given that an acoustic detection system is already provided in the apparatus, it is preferable that all or most of the required liquid properties are measured/derived from acoustic measurements. To measure the speed of sound in the liquid, the time of flight is measured over a known distance d and velocity υ is calculated as: $υ=2d/\Delta t$, where $\Delta t$ is the time interval between the reflected acoustic echoes from two known surfaces in the liquid. However, in an open ended container, the free surface 46 of the liquid cannot be used as one of the known surfaces because the distance between the lens 58 and the free surface 46, and the sound velocity are both unknown. To get a measurement over a fixed distance d, the calibration surface 48 (shown in FIGS. 1, 2, 6 and 7) may be inserted in the path of the acoustic beam at a known distance d away from the lens 58 of the acoustic transducer 28.

The calibration surface 48 generally is a step change added to the nozzle 34 of the liquid container 24 such that the calibration surface 48 intercepts part of the focused acoustic beam. The reflected acoustic waves from the lens 58 and the calibration surface 48 are used to determine the sound velocity in the liquid using the time of flight method. The calibration surface 48 can have many shapes. In one variation, as shown in FIG. 1, the calibration surface 48 comprises a step inside the nozzle 34 that is recessed from the top of the nozzle 34 and extends down to the orifice 42 at the end of the nozzle 34. Since the nozzle 34 is cylindrical in shape, the calibration surface 48 is also cylindrical.

Figure 6:
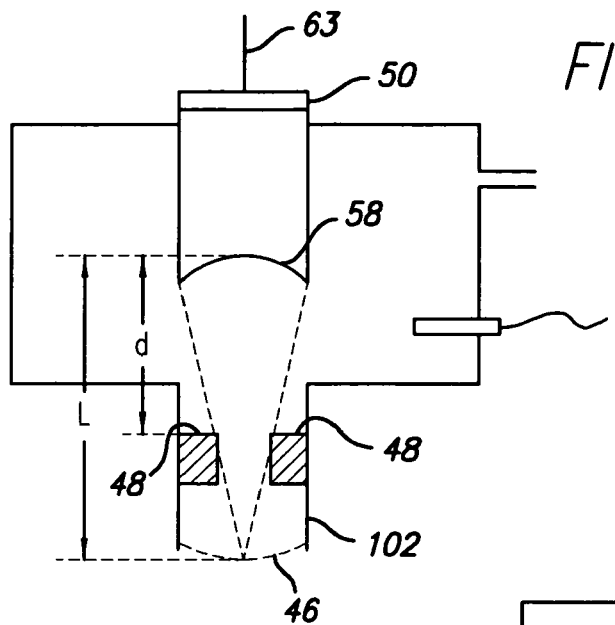
FIG. 6 illustrates an acoustic liquid dispensing apparatus showing a calibration surface.
Figure 7:
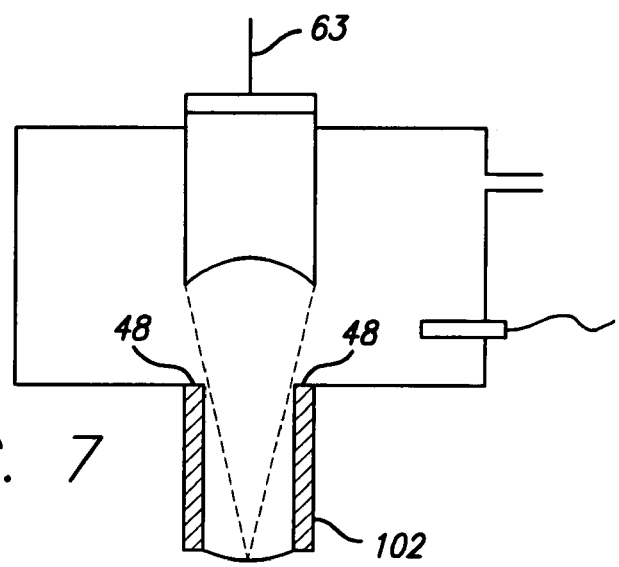
FIG. 7 illustrates another variation in the placement of calibration surface, where the side wall of the liquid nozzle is narrowed to form the liquid calibration surface.

FIG. 6 shows a variation of the calibration surface 48 in which the step is recessed from the top of the nozzle 34, but does not extend down to the orifice 42. The distances "L" and "d" are also illustrated in FIG. 6. The distance L is the distance from the lens 58 to the free surface 46. The time required for an acoustic signal to travel the distance L is referred to as $\Delta t$(lens to liquid) The distance d is the distance from the lens 58 to the calibration surface 48. The time required for an acoustic signal to travel the distance d is referred to as $\Delta t$(lens to step). In another variation, as shown in FIG. 7, the step extends along the entire length of the nozzle 34. In all of these embodiments, the calibration surface 48 must be sized (and positioned) so that it intercepts enough of the focused acoustic beam to cause a reflected wave, but does not block so much of the focused acoustic beam that there is not enough acoustic energy delivered to the free surface 46 to produce drops of source liquid.

From the above discussion, it is clear that the distance d from the lens 58 to the calibration surface 48 must be known. During manufacturing of the system 20, the distance d can be fixed to within a certain tolerance (generally about plus or minus thirty micrometers). A more precise determination of the distance d is made by filling the container 24 with a calibration fluid (such as water) for which the sound velocity (υ) is known as a function of temperature. Then the distance d can be calculated precisely from the equation $d=υ\Delta t$(lens to step)/2, where $\Delta t$(lens to step) is the time interval of the acoustic echoes between the lens and the calibration surface 48. The temperature of the calibration fluid (usually room temperature) must also be measured so that an appropriate value for the sound velocity υ is used. Once a precise determination of the distance d has been made, the speed of the acoustic beam propagating through any source liquid within the liquid container 24 can be determined through $υ=2d/\Delta t$ (lens to step); where d is the distance from the lens 58 to the calibration surface 48, as previously determined; and $\Delta t$(lens to step) is the time interval between the lens echo and the step echo, as is illustrated below with respect to FIG. 8.

Figure 8:
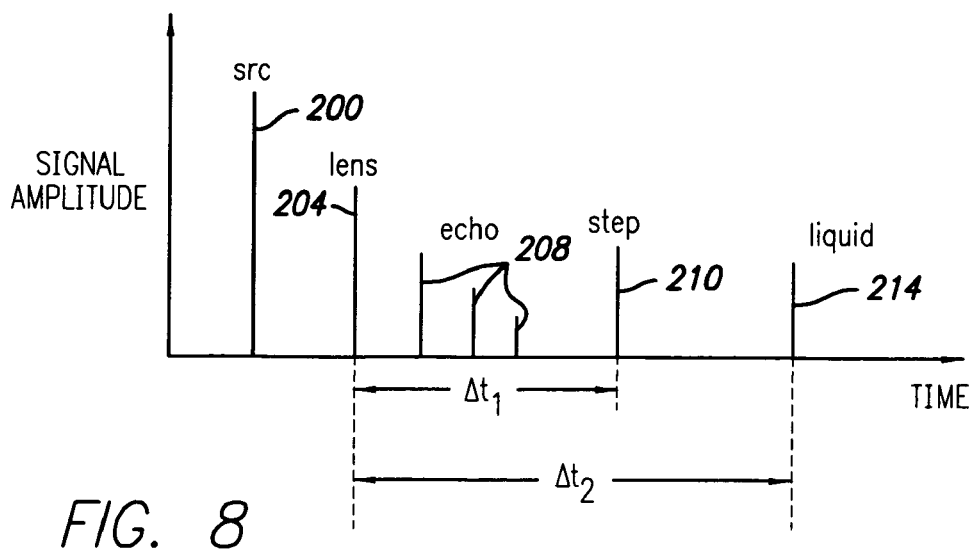
FIG. 8 is a chart illustrating the reflected acoustic waves received by the acoustic transducer.

FIG. 8 illustrates the processed signal amplitudes of the acoustic reflections detected by the piezoelectric crystal 50 (and the receiver 64) after the propagation of a single acoustic wave burst. A signal 200 (src) represents the source signal from the initial acoustic wave burst generated by the piezoelectric crystal 50. A signal 204 (lens) is the acoustic reflection/echo from the lens 58 on the waveguide 54. Following the signal 204 is a series of echoes 208 that are internal reflections from within the waveguide 54. There are usually some internal reflections after the signals 210 and 214 which are not shown in FIG. 8. A signal 210 (step) is the acoustic reflection/echo coming from the calibration surface 48, and a signal 214 (liquid) is the acoustic reflection/echo coming from the liquid free surface 46 at the distal end of the nozzle 34. The time interval between the signal 204 and the signal 210 is $\Delta t$(lens to step) or $\Delta t_1$ in FIG. 8. The time interval between the signal 204 and the signal 214 is $\Delta t$(lens to liquid) or $\Delta t_2$ in FIG. 8.

Typically, $\Delta t$(lens to step) is measured by processing the reflected signals. Similarly, $\Delta t$(lens to liquid) is measured by processing the reflected signals. Both of these calculations assume that the lens echo (signal 204) is detectable. However, in some cases, the signals 200 and 204 may overlap. This is because the length of the waveguide 54 and the speed of sound in the waveguide material determine the time between the signal 200 and the signal 204. The length of the waveguide is the distance between the proximal end of the waveguide, where the crystal 50 is acoustically connected, and the distal end where the lens 58 is positioned, the distance being to the mean effective lens position. The shorter the waveguide 54, or the faster the speed of sound of the waveguide material, the closer the signal 204 will be to the signal 200. The additional echoes 208, 210, and 214, will retain their time relationship relative to the signal 204. Signals 200 and 204 may blend together with a sufficiently short waveguide and/or faster speed of sound. In such cases, while the lens echo (signal 204) may not be easily determined, the time of the source burst (signal 200) is easily determined and the lens echo time can be calculated relative to the source burst knowing the waveguide length and the speed of sound in the waveguide material (e.g. time of the lens echo=waveguide length/speed of sound)

The estimation can be more accurately made when the temperature of the waveguide during the measurement is known along with the thermal coefficient of expansion of the material and the speed of sound thermal coefficient. The temperature sensor 78 of FIG. 1 can provide such information since the waveguide is in intimate contact with the fluid being measured by the temperature sensor. In the preferred embodiment, the time intervals $\Delta t$(lens to step) and $\Delta t$(lens to liquid) are determined by reference to the actual lens echo (signal 204). However, in alternative embodiments, the calculated time of the lens echo can be used instead of the actual lens echo as was described above.

An example of a method for calculating a fluid parameter, such as the sound velocity in a liquid, using the time interval $\Delta t$(lens to step) comprises the following steps: A test waveform is propagated from the acoustic transducer 28 through a liquid contained in a container and towards a free surface 46 of the liquid, the test waveform comprising a short burst of acoustic energy generated by a piezoelectric crystal 50 positioned at a proximal end of the acoustic transducer that is focused by a lens 58 positioned at a distal end of the acoustic transducer. A step reflected wave (signal 210) is generated by reflecting a portion of the test waveform off a calibration surface 48 positioned between the acoustic transducer and the free surface, the calibration surface being positioned at a known distance from the lens. A first period of time is determined that corresponds to the time interval for the step reflected wave to travel from the lens to the calibration surface and back to the lens. Then the sound velocity in the liquid is calculated by using twice the known distance of the calibration surface from the lens and the first period of time. In this example, the first period of time can be determined in several ways, such as by measuring the time interval Δt(lens to step) between the signals 204 and 210, or by calculating the time of the lens echo and then using the interval between the calculated time of the lens echo and the signal 210.

In a method in which the time interval Δt(lens to step) between the signals 204 and 210 is measured, the method given above could also include the following steps: Before generating the step reflected wave, generating a lens reflected wave by reflecting a portion of the short burst of acoustic energy off the lens in the acoustic transducer. After generating the step reflected wave, detecting the lens reflected wave and the step reflected wave with the piezoelectric crystal. And, using the time interval between when the lens reflected wave is detected by the piezoelectric crystal and when the step reflected wave is detected by the piezoelectric crystal in determining the first period of time. The equation $\upsilon = 2d/\Delta t$(lens to step) described previously can be used to calculate the sound velocity.

Once the velocity of the acoustic beam traveling in the liquid contained within the liquid container 24 is determined, other parameters such as the liquid level and liquid concentration may be determined through additional measurements and/or derivation. With $\upsilon$ known, the liquid level (i.e. the distance L from the lens 58 to the free surface 46) can be easily determined with $L = \upsilon \Delta t$(lens to liquid)/2.

Since there is a direct relationship between concentration and the sound velocity, once the sound velocity versus the concentration is characterized, concentration of the source liquid can be determined from the measured sound velocity. Preferably, concentration is measured by first measuring the temperature of the liquid in the container 24; such as with the temperature sensor 78. Then the concentration of a substance in the liquid is determined by comparing the sound velocity in the liquid to a table that lists the sound velocity in the liquid versus concentration for the temperature of the liquid in the container. The table of velocity versus concentration can be stored in the computer 80 so that the whole determination of concentration can be done by the computer 80.

The liquid acoustic impedance, $Z_f$, can be determined from the following relationships: $Z_f = Z_{wg}(1+R1)/(1-R1)$. $Z_{wg}$ is the acoustic impedance of the waveguide 54, which is predetermined from the material properties of the waveguide 54. R1 is the reflection coefficient of the lens/liquid interface, and $R1 = k(A_{lens1}/A_{src})$, where k is the loss factor; $A_{lens1}$ is the amplitude of the lens acoustic echo signal with liquid present in the container 24; and $A_{src}$ is the amplitude of the source acoustic signal at the receiver 64 (see FIG. 8). To determine the loss factor which relates the signal loss from the crystal 50 to the lens 58 and back, the reflected lens echo ($A_{lens0}$) can be measured with no liquid. Under this condition, R (no liquid)=−1, thus:

$$R(\text{no liquid}) = k(A_{lens0}/A_{src}) = -1$$

$$k = -A_{src}/A_{lens0}; \text{ so substitution yields:}$$

$$R1 = -A_{lens1}/A_{lens0}$$

$A_{lens0}$ is the lens acoustic echo amplitude with air in the container 24. Once R1 is determined, $Z_f$ can be calculated.

Liquid density, $\rho$, can be calculated as follows: $\rho = Z_f/\upsilon$. Ultrasonic attenuation, a, is the attenuation of the sound wave in the liquid. To make this measurement, the liquid level is kept at a given distance to the lens to avoid any changes due to change in lens to liquid surface distance. $a = \frac{1}{2}L \cdot 20 \log$ [calculated $(A_{liquid}/A_{lens})$/measured $(A_{liquid}/A_{lens})$] $A_{liquid}$ is the liquid free surface echo amplitude, and $A_{lens}$ is the lens echo amplitude with liquid, as shown in FIG. 8. The measured amplitudes are obtained by processing the amplitude signals for $A_{liquid}$ and $A_{lens}$. The calculated quantity is derived by noting that $A_{liquid}/A_{lens} = (1-R1^2)R2/R1$, where R2 is the reflection coefficient between the liquid and the air.

Ultrasonic viscosity, $\eta$, can be determined can be determined from the following equation: $\eta = (2 \rho a \upsilon^3/w^2)$; $\rho$ is the liquid density; a is the attenuation in liquid; $\upsilon$ is the sound velocity in the liquid; w is the frequency of the transmitted acoustic wave or beam.

The ability to determine the parameters of a given liquid in real-time has various advantages, including allowing the control system to determine the appropriate amount of energy to eject a droplet of a desired volume.

The ability to determine the sound velocity in the source liquid is used for the critical purpose of determining the liquid level parameter. The liquid level parameter refers to the position of the free surface 46 within the nozzle 34 (shown in FIG. 1). As noted previously, in order to control drop size, the free surface 46 must be within the depth of field of the lens 58. In a representative embodiment, the velocity of the focused acoustic beam traveling in the source liquid and the liquid level are determined using the methods outlined below. Once the liquid level has been determined, this information is available in the computer 80. The computer 80 determines if the liquid level is within the depth of field of the lens 58. If the liquid level is within the depth of field, then the computer 80 causes an acoustic pulse to be emitted from the acoustic transducer 28 thereby causing a drop to be ejected from the free surface 46. If the liquid level is not within the depth of field, then the computer 80 causes the liquid level to be changed so that it is within the depth of field. This can be done, for example, by causing the volume displacement device 74 to increase or decrease the pressure of the source liquid in the container 24, thereby causing the liquid level to move up or down in the nozzle 34. The computer 80 then rechecks the liquid level to determine if it is within the depth of field, and the process is repeated until the liquid level is within the depth of field.

In a representative embodiment, the steps involved in determining the velocity of the focused acoustic beam traveling in the source liquid comprise propagating a test waveform (signal 200 in FIG. 8) from the acoustic transducer 28 through the source liquid contained in the container 24 and towards the free surface 46. The test waveform comprises a short burst of acoustic energy generated by the piezoelectric crystal 50. For example, the test waveform may be generated by sending a few cycles of sine wave from the amplifier 62 to the crystal 50, whereas a waveform that causes droplet emission from the orifice 42 may comprise hundreds of cycles. During droplet emission, the test waveform can be generated at different intervals to check the fluid parameters. For example, the test waveform may be generated every ten to twenty drops.

The piezoelectric crystal 50 is positioned at a proximal end of the acoustic transducer 28 and the short burst of acoustic energy is focused by the lens 58 positioned at a distal end of the acoustic transducer 28. A first reflected wave (signal 204 in FIG. 8) is generated by reflecting a portion of the short burst of acoustic energy off an inside surface of the lens 58. A second reflected wave (signal 210 in FIG. 8) is generated by reflecting a portion of the test waveform off the calibration surface 48 positioned between the acoustic transducer 28 and the free surface 46. The calibration surface 46 is positioned at a known calibrated distance from the lens 58, for example by using the water calibration method described previously. The first reflected wave and the second reflected wave are detected at the piezoelectric crystal 50 which converts acoustic energy back to electrical energy. The electrical signals are sent to the receiver 64 over the transmission line 63.

The first period of time ($\Delta t_1$ in FIG. 8) is determined, where the first period of time corresponds to one half of the time interval between when the first reflected wave is detected by the piezoelectric crystal 50 and when the second reflected wave is detected by the piezoelectric crystal 50. Finally, the velocity of the test waveform in the liquid is calculated by dividing the known distance of the calibration surface 48 from the lens 58 by the first period of time. This calculation is usually done by the computer 80.

In a representative embodiment, the steps involved in determining the liquid level comprise first determining the velocity of the focused acoustic beam as was described above. In addition, a third reflected wave (signal 214 in FIG. 8) is generated by reflecting a portion of the test waveform off the free surface 46 and detecting the third reflected wave with the piezoelectric crystal 50. The crystal 50 converts the acoustic energy of the third reflected wave back into electrical energy and the electrical signal is sent to the receiver 64 over the transmission line 63.

The second period of time ($\Delta t_2$ in FIG. 8) is determined, where the second period of time corresponds to one half of the time interval between when the first reflected wave is detected by the piezoelectric crystal 50 and when the third reflected wave is detected by the piezoelectric crystal 50. Finally, the distance of the free surface 46 from the lens 58 is calculated by multiplying the velocity of the test waveform in the liquid by the second period of time. This calculation is usually done by the computer 80.

In addition to determining the liquid level, the apparatus 20 may use one or more of the real-time parameters discussed above for other purposes, such as to adjust the amount of liquid to be dispensed by the apparatus 20. In general, when one of the real-time parameters (density, concentration, viscosity, attenuation or temperature) or the liquid level, are outside of a desired range, a correction can be made by changing the amount of energy applied to the acoustic transducer to vary or control the total volume of the source liquid to be ejected from the apparatus 20.

For example, a biological compound may be placed within a DMSO solution for transfer into the various wells in a target wellplate. The liquid may contain only 3% biological compound while 97% of the solution is DMSO. However, DMSO may evaporate continuously and thus changing the concentration of the biological compound within the liquid over time. Thus to transfer a precise amount of the biological compound into various wells in a wellplate, the system would need to determine the concentration (C) of the biological compound within the DMSO liquid on a regular basis, in order to adjust the dispensing volume to compensate for the change in the concentration of the biological compound due to the loss of DMSO liquid. One of ordinary skill in the art having the benefit of the disclosure herein would appreciate that the method and apparatus described herein may be adapted to monitor and compensate for various changes over time in the source liquid.

The sound velocity measurement method described above allows one to determine the velocity of the liquid utilizing a single acoustic transducer. Once the sound velocity is determined, other parameters can also be driven directly or by utilizing other acoustic reflection data collected through the acoustic transducer. Although in this example the liquid parameter measurement technique is utilized in a liquid dispensing mechanism, one of ordinary skill in the art, having the benefit of this disclosure, would appreciate that the same method can be applied in other liquid container having an acoustic transducer and a calibration surface to measure the various parameters of the liquid in the container.

Figure 9:
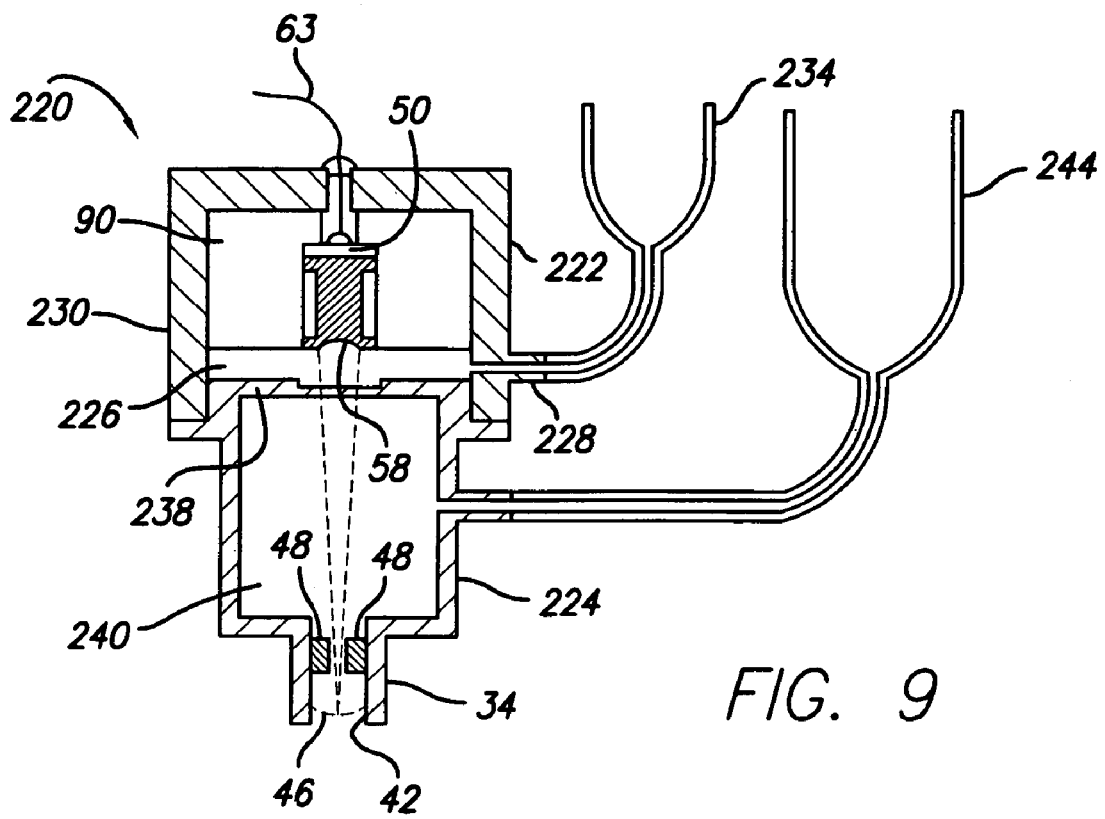
FIG. 9 is a schematic cross-sectional view illustrating another variation of an acoustic liquid dispensing apparatus according to the present invention.

In addition to the embodiments of the apparatus 20 shown in FIGS. 1-7, other variations of the apparatus 20 are possible to address specific problems faced by end users. For example, is sometimes desirable to prevent the acoustic transducer 28 from contacting the source liquid. FIG. 9 illustrates an acoustic liquid dispensing apparatus 220 that comprises a coupling medium for transmitting acoustic beam from an acoustic module 222 that contains the acoustic transducer 28, to a liquid container 224 that contains the source liquid. The use of the coupling medium allows easy removal and attachment of the liquid container 224 to the acoustic module 222 while at the same time ensuring that a quality acoustic conduit is established every time a new liquid container 224 is attached to the apparatus 220. Preferably a liquid is used as the coupling medium. However, one of ordinary skill in the art would appreciate that the coupling medium may comprise of other acoustic conductive materials. A liquid chamber 226 containing the coupling liquid is connected to a port 228 on a primary housing 230 of the apparatus 220. A removable liquid receptacle 234 is attached to the port 228 at the base of the primary housing 230.

A proximal wall 238 of the liquid container 224 fits tightly into the module 222 to form a liquid tight seal for the chamber 226. A cavity 240 inside the container 224 holds the source liquid. The container 224 includes the nozzle 34 and the orifice 42. The coupling liquid is directed into the chamber 226 between the lens 58 of the acoustic transducer 28 and the wall 238 such that the focused beam generated by the acoustic transducer 28 will be transmitted through the coupling liquid, the proximal wall 238, the source liquid in the cavity 240, and towards the free surface 46 in the nozzle 34. An external receptacle 244 directs a supply of source liquid into the cavity 240. Like the external receptacle 70 (described previously with respect to FIG. 1), the receptacle 244 may include a displacement mechanism to control the supply of the coupling liquid into the cavity 240 and/or to control the liquid level of the free surface 46. Similarly, a calibration surface 48 may be included in the nozzle 34 of the container 224.

Figure 10:
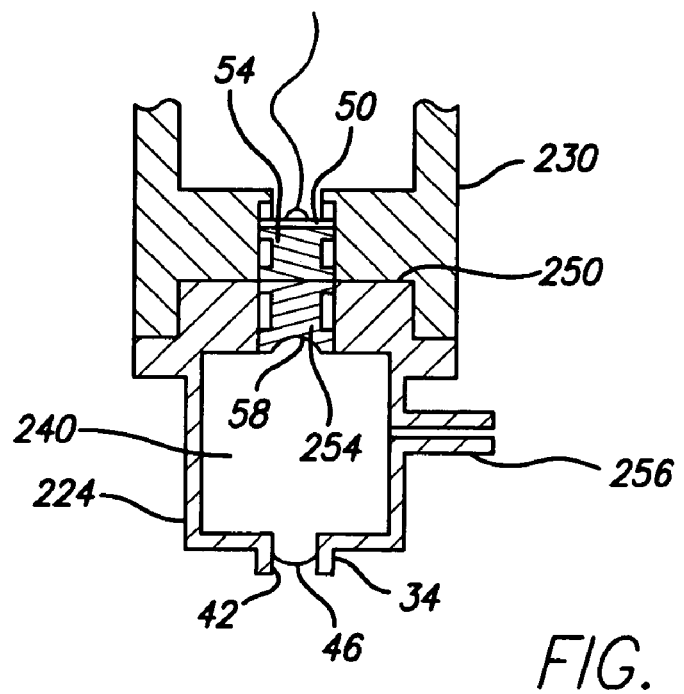
FIG. 10 is a schematic cross-sectional view illustrating another variation of an acoustic liquid dispensing apparatus according to the present invention.

FIG. 10 illustrates another approach to separating the liquid container 224 from the acoustic module 222. This allows the source liquid to be changed without contaminating the acoustic module 222. The acoustic module 222 includes an acoustic transducer 249 (comprised of the crystal 50 and the waveguide 54, but not the lens 58). The module 222 is configured with an interface 250 for receiving the liquid container 224. Locking joints, matching threads, or other attachment mechanisms may be provided to secure the liquid container 224 to the module 222. The acoustic wave emitted by the acoustic transducer 249 is transmitted across the interfacing 250 to a second waveguide 254 that includes the lens 58. A focused acoustic beam is emitted from second waveguide 254, passes through source liquid contained in the cavity 240, and is focused onto the liquid free surface 46 in the orifice 42 of the nozzle 34.

The distal end of the waveguide in the transducer 249 is machined into a flat surface for interfacing with a proximal end of the waveguide 254. The waveguide 254 is embedded in a wall of the detachable liquid container 224. The proximal end of the second waveguide 254 is machined to match the distal end of the waveguide in the base unit. When the removable liquid container 224 is attached to the acoustic module 222, the two waveguides connect and form a continuous path to facilitate the propagation of the acoustic wave or beam from the piezoelectric crystal 50 to the orifice 42 in the nozzle 34. A gel can be positioned between the waveguide 254 and the waveguide 54 to facilitate acoustic coupling. An optional port 256 may be provided on the removable container 224 for supplying a source liquid into the cavity 240. The external receptacle 244 (shown in FIG. 9) could be attached to the port 256.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

We claim:

1. A method for acoustically measuring one or more fluid parameters comprising:
propagating a test waveform from an acoustic transducer through a liquid contained in a container and towards a free surface of the liquid, the test waveform comprising a short burst of acoustic energy generated by a piezoelectric crystal positioned at a proximal end of the acoustic transducer that is focused by a lens positioned at a distal end of the acoustic transducer;
generating a step reflected wave by reflecting a portion of the test waveform off a calibration surface positioned between the acoustic transducer and the free surface, the calibration surface being positioned at a known distance from the lens;
determining a first period of time that corresponds to the time interval for the step reflected wave to travel from the lens to the calibration surface and back to the lens; and
calculating a sound velocity in the liquid by using twice the known distance of the calibration surface from the lens and the first period of time.

2. The method of claim 1 further comprising:
generating a lens reflected wave by reflecting a portion of the short burst of acoustic energy off the lens in the acoustic transducer;
detecting the lens reflected wave and the step reflected wave with the piezoelectric crystal; and
using the time interval between when the lens reflected wave is detected by the piezoelectric crystal and when the step reflected wave is detected by the piezoelectric crystal in determining the first period of time.

3. The method of claim 1 further comprising:
generating a liquid reflected wave by reflecting a portion of the test waveform off the free surface of the liquid;
detecting the liquid reflected wave with the piezoelectric crystal;
determining a second period of time that corresponds to the time interval for the liquid reflected wave to travel from the lens to the free surface and back to the lens; and
calculating the distance of the free surface from the lens by using the sound velocity in the liquid and the second period of time.

4. The method of claim 3 further comprising:
based on the distance of the free surface from the lens, changing an amount of energy applied to the acoustic transducer to control the size of a droplet of the liquid to be ejected from the free surface.

5. The method of claim 1 further comprising:
measuring the temperature of the liquid in the container; and
determining the concentration of a substance in the liquid by comparing the sound velocity in the liquid to a table that lists the sound velocity in the liquid versus concentration at the temperature of the liquid in the container.

6. The method of claim 5 further comprising:
based on the concentration of the substance in the liquid, changing an amount of energy applied to the acoustic transducer to control the size of a droplet of the liquid to be ejected from the free surface.

7. A method for acoustically measuring one or more fluid parameters comprising:
propagating a test waveform from an acoustic transducer through a liquid contained in a container and towards a free surface of the liquid, the test waveform comprising a short burst of acoustic energy generated by a piezoelectric crystal positioned at a proximal end of the acoustic transducer that is focused by a lens positioned at a distal end of the acoustic transducer;
generating a lens reflected wave by reflecting a portion of the short burst of acoustic energy off the lens in the acoustic transducer;
generating a step reflected wave by reflecting a portion of the test waveform off a calibration surface positioned between the acoustic transducer and the free surface, the calibration surface being positioned at a known distance from the lens;
generating a liquid reflected wave by reflecting a portion of the test waveform off the free surface of the liquid;
detecting the lens reflected wave, the step reflected wave and the liquid reflected wave with the piezoelectric crystal;
determining a first period of time that corresponds to the time interval between when the lens reflected wave is detected by the piezoelectric crystal and when the step reflected wave is detected by the piezoelectric crystal;
determining a second period of time that corresponds to the time interval for the liquid reflected wave to travel from the lens to the free surface and back to the lens;
calculating a sound velocity in the liquid by using the known distance of the calibration surface from the lens and the first period of time; and
calculating the distance of the free surface from the lens by using the sound velocity in the liquid and the second period of time.

8. The method of claim 7 further comprising:
based on the distance of the free surface from the lens, changing an amount of energy applied to the acoustic transducer to control the size of a droplet of the liquid to be ejected from the free surface.

* * * * *